United States Patent [19]
Fujii et al.

[11] 3,931,241
[45] Jan. 6, 1976

[54] METHOD FOR PREPARATION OF CITRACONIC ACID AND DERIVATIVES THEREOF

[75] Inventors: Chiyuki Fujii; Yoshio Kosai; Iwao Kibayashi, all of Machida, Japan

[73] Assignee: Denki Kagaku Kogyo Kabushiki Kaisha, Tokyo, Japan

[22] Filed: Aug. 30, 1974

[21] Appl. No.: 501,959

[30] Foreign Application Priority Data
Aug. 31, 1973 Japan.............................. 48-98040

[52] U.S. Cl... 260/346.8 R; 260/485 R; 260/537 N; 260/544 Y
[51] Int. Cl.$^2$....................................... C07D 307/60
[58] Field of Search ........ 260/346.8, 485, 537, 540, 260/544

[56] References Cited
UNITED STATES PATENTS
3,770,812  11/1973  Blood et al. .................... 260/346.8

Primary Examiner—Harry I. Moatz
Attorney, Agent, or Firm—Sughrue, Rothwell Mion Zinn Macpeak

[57] ABSTRACT

A method of preparing citraconic acid and derivatives thereof comprising reacting methylsuccinic acid and derivatives thereof (such as an acid halide, an acid anhydride, a monoester and a diester) with chlorine in the absence of or in the presence of a catalyst at a temperature ranging from about 100° to 500°C.

5 Claims, No Drawings

METHOD FOR PREPARATION OF CITRACONIC ACID AND DERIVATIVES THEREOF

BACKGROUND OF THE INVENTION

1. Field of the Invention

This invention relates to a method for preparation of citraconic acid and derivatives thereof, and more precisely, to a method for preparation of citraconic acid and derivatives thereof by reacting methylsuccinic acid and derivatives thereof with chlorine.

2. Description of the Prior Art

Citraconic acid and derivatives thereof per se are useful compounds, and, in particular, they are of special interest as raw materials for producing itaconic acid since they can easily be converted to itaconic acid.

For the synthesis of citraconic acid, some conventional processes, including the pyrolysis of citric acid (as described in U.S. Pat. No. 3,701,805) and the direct oxidation of isoprene (as described in Japanese Pat. Publication No. 38425/72) are known. However, these conventional means involve some problems with respect to formation of by-products, and with respect to yield, purity and cost of the products.

The synthesis of citraconic acid has been investigated in detail to overcome the defects in the prior art, and a method for preparation of citraconic acid and derivatives thereof which does not have the defects described above has been developed.

SUMMARY OF THE INVENTION

Accordingly, this invention provides a method for preparation of citraconic acid and derivatives thereof comprising chlorinating methylsuccinic acid and derivatives thereof. In the present method, citraconic acid and derivatives thereof are directly formed under reaction conditions where the chlorinating reaction proceeds.

The reaction with chlorine (or dehydrogenating reaction) also proceeds utilizing the anhydride, chloride or esters of methyl succinic acid as starting materials at a temperature ranging from about 100° to 500°C. By hydrolizing the formed anhydride, citraconic acid can easily be accomplished.

DETAILED DESCRIPTION OF THE INVENTION

Derivatives of methylsuccinic acid which can be used in the present invention include methylsuccinic acid monohalide and dihalide, methylsuccinic acid anhydride, and methylsuccinic acid monoesters and diesters. Suitable esters are preferably those with aliphatic alcohols having 1 to 8 carbon atoms and with aromatic alcohols, e.g., 2-chloroethanol, benzyl alcohol, etc. The method of this invention can employ methylsuccinic acid, a derivative thereof or a mixture thereof as a starting material(s)

The reaction of methylsuccinic acid and derivatives thereof with chlorine can be carried out in the absence of or presence of a catalyst at a temperature of about 100° to 500°C, and it is preferred to carry out the chlorinating reaction at a temperature of 140°C or above in order to accelerate the reaction rate. On the other hand, it is preferred to carry out the reaction at a temperature of 400°C or below to prevent the formation of undesirable by-products resulting from the pyrolysis of methylsuccinic acid and derivatives thereof (starting materials) and citraconic acid and derivatives thereof (products).

The reaction can be carried out in a liquid-phase or a gasphase at a temperature within the above-described range.

The present reaction sufficiently proceeds without the presence of a catalyst, but catalysts which are usually used in chlorination reactions and dehydrochlorination reactions, as long as they do not hinder the reaction, can be employed, if desired. The catalyst, where used, can be suspended in a liquid medium or supported on a suitable carrier. A suitable amount of the catalyst generally ranges from about 0.01 to 1000 times by weight the amount of the methylsuccinic acid and derivatives thereof.

Examples of catalysts which can be used in the present reaction include halides of phosphorus, iodine, sulfur, iron, aluminum, nickel and copper, the oxychloride of sulfur (thionylchloride) and anhydrides and halides of organic acids (e.g., having 2 to 10 carbon atoms, such as acetic acid, monochloroacetic acid, dichloroacetic acid, trichloroacetic acid and trifluoroacetic acid).

It also is possible to carry out the reaction in a reactor filled with a non-reactive filler optionally having the catalyst adsorbed thereon or admixed therewith.

The present reaction can be carried out under at superatmospheric pressures, normal pressure or subatmospheric pressures. Chlorine can be recovered from the hydrogen chloride generated in the reaction by conversion using a conventional dehydrating process and can then be circulated for re-use. The molar ratio of methylsuccinic acid and derivatives thereof to the chlorine can vary, e.g; from a trace amount when the reaction is conducted in the liquid phase to about 0.1 to 10 times the amount of the chlorine when the reaction is conducted in the gaseous phase, and the time required for the contact of the methylsuccinic acid and derivatives thereof with chlorine gas can be about 0.1 second or more.

When the reaction is carried out as a liquid-phase reaction, direct chlorination in the absence of a solvent is possible, but it also is possible to use a solvent which is inert to chlorine under the reaction condition, such as halogenated hydrocarbons, e.g; carbon tetrachloride, halogenated carboxylic acids, e.g., trichloroacetic acid, carboxylic acid halides or halides or oxyhalides of sulfur or phosphorus, e.g., sulfuryl chloride, etc.

When the reaction is carried out as a gas-phase reaction, a diluting gas (such as nitrogen, carbon dioxide, helium, argon, carbon tetrachloride, Freon (trade name of E. I. du Pont de Nemours, & Co. Inc.), etc.) can be used for diluting the reaction system.

This invention will be explained in greater detail by reference to the following Examples, but the invention is not to be construed as being limited to only the illustrated Examples. Unless otherwise indicated, all parts, percents, ratios and the like are by weight.

EXAMPLE 1

10g of methylsuccinic acid anhydride was placed in a stainless reactor equipped with a reflux condenser (water cooling type), and 8g of chlorine gas were fed thereinto under atmospheric pressure and at a constant feeding rate over the course of 2 hours while maintaining the reaction temperature at 180°C.

After the reaction, the product was analyzed using gas chromatography, and it was found that the product contained 8.3g of citraconic acid anhydride and 0.7g of methylsuccinic acid anhydride.

The formation of chloromethylsuccinic acid anhydride (which was proved to have the following formula) was observed as a byproduct and the yield thereof was about 10 mol% of the citraconic acid anhydride.

$$CH_3-CH-CH-Cl$$
$$O=C\quad\quad C=O$$
$$\diagdown O \diagup$$

EXAMPLE 2

10g of methylsuccinic acid was placed in a stainless reactor provided with a reflux condenser (water cooling type), 0.2g of phosphorus chloride was added thereto, and 7.5g of chlorine gas were fed thereinto under atmospheric pressure and at a constant feeding rate over the course of 3 hours while maintaining the reaction temperature at 220°C.

After completion of the reaction, the reaction product was analyzed using gas chromatography, and it was found that the product contained 5.8g of citraconic acid anhydride and 2.1g of methylsuccinic acid anhydride.

It was further confirmed that chloromethylsuccinic acid anhydride (the same compound as in Example 1) was formed in an amount of 6 mole% of the yield of the citraconic acid anhydride.

EXAMPLE 3

10g of dimethyl methylsuccinate was placed in the same reactor as in Example 1, 1.0g of ferric chloride was added thereto, and 5.0g of chlorine gas were fed thereinto under atmospheric pressure and at a constant feeding rate over the course of 1 hour while maintaining the reaction temperature at 170°C.

After completion of the reaction, the resulting product was analyzed using gas chromatography, and it was confirmed that 1.0g of dimethyl citraconate and 0.6g of citraconic acid anhydride were formed.

EXAMPLE 4

10g of methylsuccinic acid anhydride was placed in the same reactor as in Example 1, and 4g of chlorine gas diluted with nitrogen were fed and circulated therein under atmospheric pressure and at a constant feeding rate over the course of 1 hour while maintaining the reaction temperature at 180°C.

Next, the reacted gas was passed through a layer in a Pyrex tube (diameter: 2.5cm) packed with 20cc of an oxychlorinating catalyst comprising silica-alumina carrying 5% by weight of potassium chloride and 5% by weight of cupric chloride, at a temperature of 250°C while introducing oxygen in an amount of 1000cc/hour. The water generated was trapped in a vessel and the chlorine gas recovered was circulated, whereby the reaction was carried out for 2 hours. After completion of the reaction, the product was analyzed using gas chromatography, and it was confirmed that the product contained 7.4g of citraconic acid anhydride and 1.8g of methylsuccinic acid anhydride. In addition, a small amount of chloromethylsuccinic acid anhydride was formed.

EXAMPLES 5–10

In each of these Examples, the same process as in Example 1 was carried out with the exception that 1g of each catalyst as shown in the following Table 1 was used and the reaction temperature used was as shown in the same Table 1. A glass-lined autoclave was used in Example 9. The results obtained are shown in Table 1.

Table 1

| Ex. No. | Kind of Catalyst | Reaction Temperature (°C) | Yield of Citraconic Acid Anhydride (g) |
| --- | --- | --- | --- |
| 5 | Acetic Acid Anhydride | 180 | 9.0 |
| 6 | Monochloroacetic Acid | 160 | 8.1 |
| 7 | Cupric Chloride | 180 | 8.5 |
| 8 | Aluminum Chloride | 160 | 7.9 |
| 9 | Thionyl Chloride | 150 | 8.4 |
| 10 | Nickel Chloride | 200 | 8.9 |

EXAMPLE 11

20ml of α-alumina supporting 10% of copper chloride was charged in a reaction tube made of Pyrex glass having a diameter of 20mm. A mixed gas of methylsuccinic acid anhydride, chlorine and nitrogen in a molar ratio of 2:1:12 was passed through the tube at a temperature of 260°C and at a space velocity of 500hr$^{-1}$ under normal pressure to obtain citraconic acid anhydride in an amount of 81 mol% based on the chlorine used.

While the invention has been described in detail and with reference to specific embodiments thereof, it will be apparent to one skilled in the art that various changes and modifications can be made therein without departing from the spirit and scope thereof.

What is claimed is:

1. A method for the preparation of citraconic acid and derivatives thereof comprising reacting methylsuccinic acid, methylsuccinic acid halide, methylsuccinic acid anhyride, methylsuccinic acid monoesters or diesters wherein said esters are those with aliphatic alcohols having 1 to 8 carbon atoms and with aromatic alcohols, or a mixture thereof with chlorine at a temperature ranging from about 100° to 500°C.

2. The method as claimed in claim 1, wherein the reacting is in the presence of a catalyst selected from the group consisting of (1) the halides of a member selected from the group consisting of phosphorous, iodine, sulfur, iron, aluminum, nickel and copper, (2) the oxychloride of sulfur, and (3) the anhydrides and halides of organic acids selected from the group consisting of acetic acid, monochloroacetic acid, dichloroacetic acid, trichloroacetic acid and trifluoroacetic acid.

3. The method as claimed in claim 1, including recovering chlorine from the hydrogen chloride generated in the reaction by conversion using a dehydrating technique.

4. The method as claimed in claim 1, wherein the reaction is a liquid-phase reaction.

5. The method as claimed in claim 1, wherein the temperature ranges from 140° to 400°C.

* * * * *